(12) United States Patent
Lin et al.

(10) Patent No.: US 10,077,465 B2
(45) Date of Patent: Sep. 18, 2018

(54) SORBENTS FOR EXTRACTION AND STABILIZATION OF NUCLEIC ACIDS

(71) Applicant: The United States of America, as represented by the Secretary of the Navy, Washington, DC (US)

(72) Inventors: Baochuan Lin, Bethesda, MD (US); Brandy J. White, Washington, DC (US); Brian Melde, Alexandria, VA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 60 days.

(21) Appl. No.: 15/264,021

(22) Filed: Sep. 13, 2016

(65) Prior Publication Data

US 2018/0073052 A1    Mar. 15, 2018

(51) Int. Cl.
*C12Q 1/6806* (2018.01)
(52) U.S. Cl.
CPC .................................. *C12Q 1/6806* (2013.01)
(58) Field of Classification Search
CPC ........... C12Q 1/68; G01N 15/00; C01B 32/05
See application file for complete search history.

(56) References Cited

U.S. PATENT DOCUMENTS

| 6,673,631 B1 * | 1/2004 | Tereba ............... C12N 15/1013 423/335 |
| 8,246,999 B2 | 8/2012 | Lin et al. |
| 8,647,644 B1 | 2/2014 | Torney et al. |

OTHER PUBLICATIONS

White et al, Functionalized Organosilicate Sorbents for Air Purification, 2013, Naval Researh Laboratory reports, pp. 1-70 (Year: 2013).*
Lin et al, Adsorption and Elution of Nucleic Acids: Mesoporous Materials and Methods, 2017, The Open Access Journal of Science and Technology, 5, Article ID 101190, 18 pages (Year: 2017).*
B.J. Johnson, B.J. Melde, M.A. Dinderman, and B. Lin, "Stabilization of RNA through Absorption by Functionalized Mesoporous Silicate Nanospheres," PLoS One 7, e50356, (2012).
Slowing, I. I.; Trewyn, B. G.; Lin, V. S. Y. J Am Chem Soc 2007, 129, 8845-8849.
Melde, B. J.; Johnson, B. J.; Dinderman, M. A.; Deschamps, J. R. Microporous and Mesoporous Materials 2010, 130, 180-188.

* cited by examiner

*Primary Examiner* — Narayan K Bhat
(74) *Attorney, Agent, or Firm* — US Naval Research Laboratory; Roy Roberts

(57) ABSTRACT

Mesoporous sorbents are effective for storing and transporting nucleic acids. In particular, two ethane-bridged silica sorbents with amine functionalities are particularly effective and capable of binding nucleic acids for storage.

7 Claims, 7 Drawing Sheets

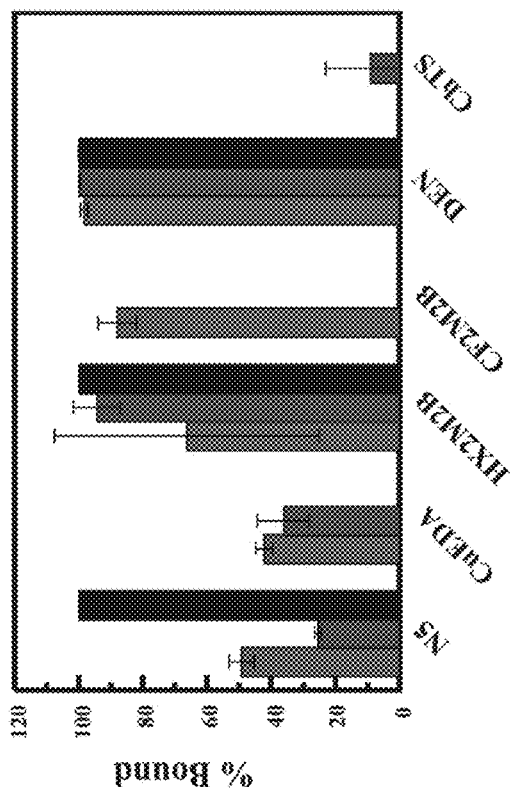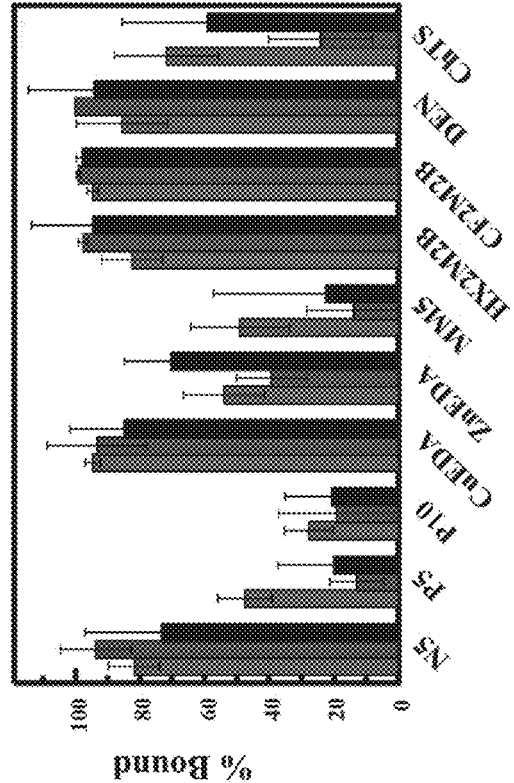
FIG. 2A
FIG. 2B

SORBENTS FOR EXTRACTION AND STABILIZATION OF NUCLEIC ACIDS

CROSS-REFERENCE TO RELATED APPLICATIONS

None.

BACKGROUND

Successful advancements in molecular diagnostics related to a wide range of fields, including medical, biological, environmental, forensics, and food safety, drives the need for preservation of nucleic acid integrity during sample collection, transportation, processing, and storage.[1] RNA tends to be more labile than DNA and can be hydrolyzed readily when exposed to conditions of high pH, metal cations, or high temperatures, as well as contaminating RNA ribonucleases (RNases). RNases are known to be present endogenously in cells, tissues, body oils, and bacteria and/or fungi in airborne dust particles, the main concern for preserving the integrity of RNA.[2] There are a number of commercial products for preservation during sample collection: RNAlater Tissue Collection: RNA Stabilization Solution (Life Technologies, Carlsbad, Calif.), RNAlater RNA Stabilization Reagent (Qiagen, Valencia, Ca), PAXgene tubes (PreAnalytix, Valencia, Calif.), and RNAstable (Biomatrica, San Diego, Calif.). Alternatively, RNA can be protected within a physical barrier employing materials similar to those used in DNA encapsulation: liposomes, micelles, or polymers.[3-6]

The most common method for maintaining nucleic acid integrity, in general, is freezing at low temperature (−20° C. or −80° C.).[9] This approach is not practical for routine specimen processing, storage, or shipping when under austere field conditions. Furthermore, the costs associated with maintaining large sets of samples under the necessary conditions over long periods of time can be prohibitive.[10-12]

To address these issues, several technologies have been developed for the stabilization and storage of nucleic acids at room temperature. These technologies are primarily based on three principles.

The first is anhydrobiosis, the dehydration process used by some organisms to survive extreme conditions.[13-14] These methods include spray drying, spray-freeze-drying, air drying, and lyophilization with or without additives (i.e. trehalose) commonly used for DNA preservation.[15-19] One study also indicated that anhydrobiosis worked well for RNA preservation.[20] While in the dry state, the matrix components form a thermo-stable barrier around the DNA protecting the sample from damage and degradation. The DNA can be recovered by rehydration as the matrix will completely dissolve.[11,21,22]

The second approach to stabilization is to use chemicals or proteins to bind nucleic acids, changing their characteristics and interactions to provide stability. Several chemicals and compounds have been reported to preserve nucleic acids at room temperature from periods of weeks to months. DNA-binding protein from starved cells (Dps) and poly(A) binding protein (Pab1p) were reported to stabilize DNA and mRNA, respectively.[12,23-38] Commercial products, such as RNAlater and Trizol (Life Technologies), are based on this approach and have been documented to stabilize nucleic acids at room temperature for long periods of time.[11,27,30,39-41]

Physically protecting nucleic acids from the environment, through encapsulation or adsorption onto a solid support, is the third of the stabilization principles and has emerged for the delivery of gene therapeutics. A range of materials, including liposomes, metal particles, polymers, potato starch, silk fibron and surfactants, have been developed with these applications in mind.[3,42-48]

Field collection of samples for molecular analysis presents distinct challenges owing to the lack of laboratory facilities and renders the preservation of nucleic acids necessary for storage and transportation. It is also critical that these approaches provide methods for recovery of the nucleic acids without contaminating downstream molecular diagnostic assays.

BRIEF SUMMARY

The invention relates to improved methods and materials applicable to the capture of nucleic acid targets from complex matrices offering subsequent stabilization of the targets in the absence of refrigeration.

A first embodiment is a nucleic acid sorbent comprising a mesoporous ethane-bridged silica selected from the group consisting of N5 and CuEDA. Optionally, the sorbent can modified by or used in combination with another stabilizing group that could be covalently attached to or mixed in with the sorbent to be associated therewith. For example, the below-described CuEDA sorbent could have trehalose covalently attached. By way of further example, bovine serum albumin (BSA) could be mixed with the below-described N5 sorbent.

Another embodiment is a method of storing nucleic acid by contacting a nucleic acid with a sorbent of the first embodiment, thereby causing the nucleic acid to releasably bind to the sorbent.

BRIEF DESCRIPTION OF THE DRAWINGS

FIGS. 2A and 2B show nucleic acid (NA) targets bound from solutions consisting of 30 μg sorbent with 300 ng of RNA (red); 3 ng NAC1 DNA (blue); or 30 ng NAC1 ssDNA (black). Sorbents were used without pre-washing (a) and following the described wash steps (b). Error bars indicate standard deviation across six measurements.

DETAILED DESCRIPTION

Definitions

Figure 1:
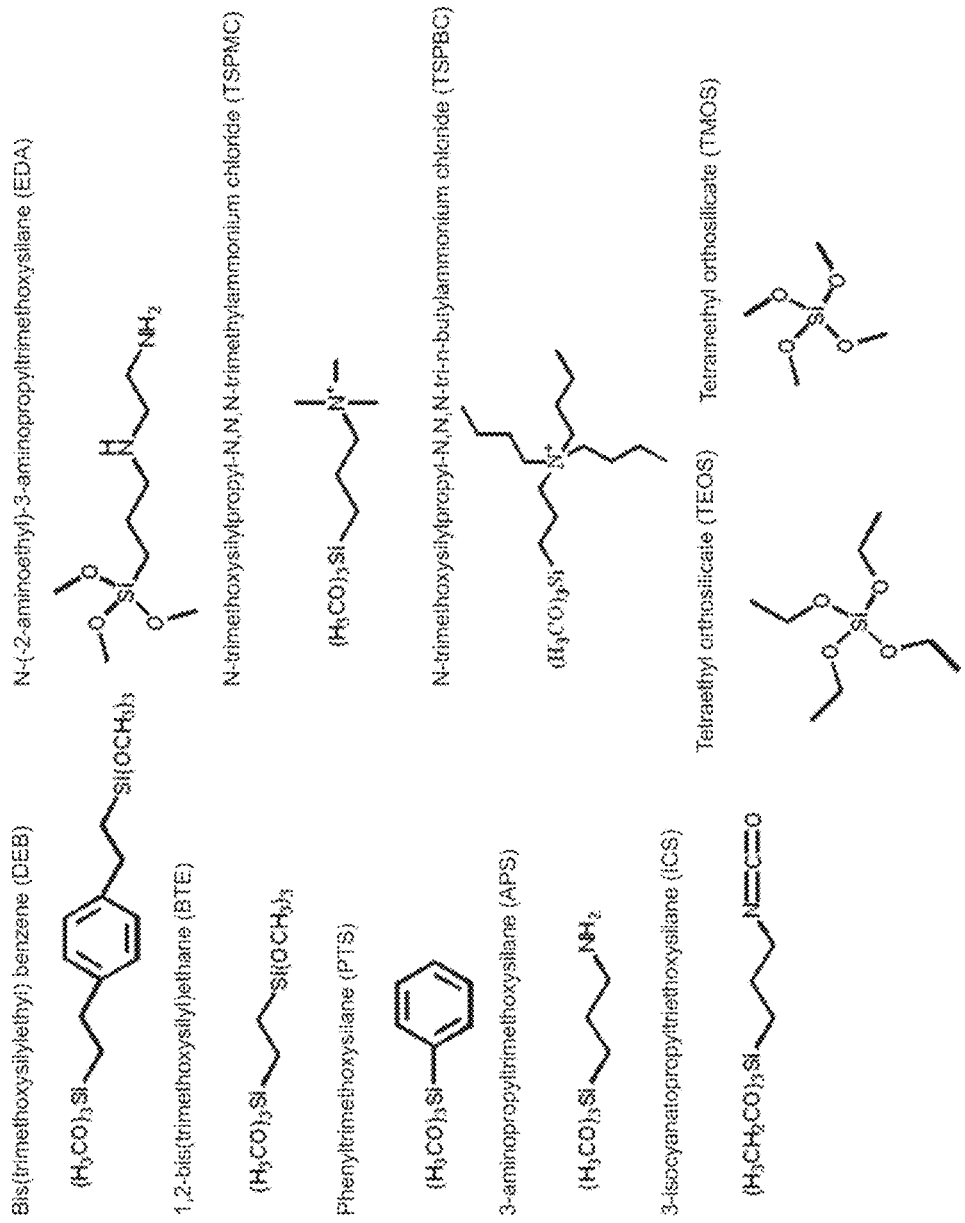
FIG. 1 shows precursors groups utilized in synthesis of sorbents.

Before describing the present invention in detail, it is to be understood that the terminology used in the specification is for the purpose of describing particular embodiments, and is not necessarily intended to be limiting. Although many methods, structures and materials similar, modified, or equivalent to those described herein can be used in the practice of the present invention without undue experimentation, the preferred methods, structures and materials are described herein. In describing and claiming the present invention, the following terminology will be used in accordance with the definitions set out below.

As used in this specification and the appended claims, the singular forms "a", "an," and "the" do not preclude plural referents, unless the content clearly dictates otherwise.

As used herein, the term "and/or" includes any and all combinations of one or more of the associated listed items.

As used herein, the term "about" when used in conjunction with a stated numerical value or range denotes somewhat more or somewhat less than the stated value or range, to within a range of ±10% of that stated.

Overview

Potential of methods utilizing encapsulation of RNA within tunable, semi-permeable structures has not been fully explored for stabilization and storage purposes. Instead, RNA encapsulation methods developed have mainly been used as delivery system for small interfering RNA (siRNA).[3,4,6-8]

Materials that allow small molecules to diffuse through while limiting the diffusion of proteins, i.e. RNases, can provide ideal environments to prevent RNA degradation resulting from exposure to chemicals or enzymes which in turn provide the potential for storing and transporting nucleic acids at room temperature in a cost-effective, environmentally friendly manner.

One example of these types of structures is mesoporous silica sorbents (MSSs). These materials offer high surface areas and ordered or semi-ordered pore structures. Similar to the MCM-41 mesoporous silicate, MSSs are often synthesized with surfactant templates to provide surface areas of up to 1,000 m2/g and ordered pore systems with narrow pore size distributions. Reaction conditions can be chosen to yield relatively monodisperse particle sizes (50-200 nm). Small particle sizes allow for capping of mesopores or other modifications that may prevent undesired release of encapsulated cargo. Nanoparticle morphologies can also offer advantages in adsorption rates and saturation loading levels.[50-53] These features have been applied to many studies of MSS materials related to biosensing and controlled delivery.[54-57] Materials of this type have been shown to provide stability to proteins through adsorption interactions as well as through covalent immobilization.[58-61]

The US Naval Research Laboratory (NRL) demonstrated RNA adsorption onto mesoporous silica sorbents (MSSs) with and without additional stabilizing reagents including common sugars and bovine serum albumin (BSA).[62] The NRL developed MSSs provided enhanced stability for extended periods allowing the adsorbed RNA to be eluted using simple buffers and employed directly for downstream molecular diagnostic assays.[63]

It can be desirable to control interactions with the nucleic acids that result in degradation. Some of these interactions are restricted through adsorption or encapsulation; for example, the access of enzymes and microorganisms as well as the mobility of the nucleic acids. Other features of interest for the sorbents are altering solvent interactions, providing reducing sites and chelating groups, and inhibiting nuclease activity.

Additional study described herein used chemical functionalities incorporated into the sorbents to provide the potential for addressing other aspects of nucleic acid degradation. Binding and elution of RNA, DNA, and single stranded DNA (ssDNA) were evaluated as well as elution of the bound material and the impact of the sorbents on long term sample viability.

The work described herein evaluated the potential of mesoporous sorbents bearing chemical functionalities for stabilization of nucleic acid targets.[64] While many of the functionalized porous materials were found to remove RNA, DNA, and ssDNA from solution, recovery of the targets from the sorbents proved challenging. The desire to avoid downstream contamination prevents the use of many harsher elution conditions. A pre-conditioning step using Triton X-100 effectively prevented the types of interactions desired with several of the surfaces considered. Other commonly used prehybridization washing solutions, such as 2×SSC with 0.1% SDS or 6×SSPE with 0.1% SDS, could offer substitutions that reduce interaction with the π-bonds of the sorbents. Of the materials that were suitable for use with the pre-conditioning step, the sorbent functionalized with primary amine groups (N5) showed promising results for RNA and ssDNA stabilization. The performance of the sorbent at room temperature was approximately equivalent to the performance of the NRL-developed trehalose incorporating sorbent at 4° C.[62] N5 showed significant stabilization of RNA even when stored at 37° C. Combinations of sugars (trehalose, glucosamine) and the functional groups considered offer the potential for further improvements in stabilization.

Synthesis of Sorbent Materials

A number of standard synthetic processes have been utilized to synthesize the various sorbents.

Mesoporous Silicate Nanoparticles.

Synthesis of the nanoparticle materials was adapted from a published procedure.[55] Briefly, 1.0 g of CTAB (cetyltrimethylammonium bromide, a cationic surfactant) was dissolved at 80° C. in 475 mL water and 7.0 mL 1.0 M NaOH with stirring. The reactor vessel was a polyethylene bottle suspended in a temperature controlled water bath. Mesitylene (6 mL) was added to the stirring surfactant solution. Tetraethyl orthosilicate (TEOS, 5.0 mL) was added dropwise, and a white precipitate formed. The mixture was stirred and heated at 80° C., collected by filtration, and allowed to dry at room temperature. As-synthesized material was refluxed in 160 mL of ethanol with 5 mL of concentrated HCl overnight. Mesoporous silicate nanoparticles were separated from the acidified ethanol by centrifugation. They were suspended in ethanol, centrifuged, and resuspended three times in water followed by centrifugation each time. Extracted sorbents were dried at 80° C.

Modification of the silicate structure by stabilizing compounds was accomplished by first providing functional groups on the silicate surface. Materials (1 g) were refluxed with the appropriate precursor (3-aminopropyltrimethoxysilane, APS or 3-isocyanatopropyltriethoxysilane, ICS; 22 µM) in toluene overnight.[65] Functionalized materials were recovered using vacuum filtration with Whatman #5 filter paper, rinsed with toluene, and dried at 110° C. For immobilization of sugars, the ICS functionalized sorbent (1 g) was placed in solution with an excess of the sugar (1 g in 0.25 L). The solution was then mixed for 48 h before the material was recovered by vacuum filtration, thoroughly rinsed with deionized water to remove excess, unbound sugar, and dried at 60° C. for 24 h. For immobilization of bovine serum albumin (BSA), EDC (1-ethyl-3-[3-dimethylaminopropyl] carbodiimide) chemistry was used. APS functionalized silicate material (1 g) was placed with 1 g BSA in a solution of 5 mM EDC in 100 mM MES buffer (2-(N-morpholino) ethanesulfonic acid; pH 5.5). The solution was incubated with agitation overnight, rinsed thoroughly with water, and dried at 50° C. for 24 h.

BTE and DEB-Based Materials.

Synthesis of the bis(trimethoxysilylethyl)benzene (DEB) and 1,2-bis(trimethoxysilyl)ethane (BTE) based sorbents (MM5, P10, P5, N5, and DEN) was based on a previously described approach[49,66,67] and began with dissolving mesitylene 98% (1,3,5-trimethylbenzene or TMB) and Pluronic® P123 (1.9 g) in 0.1 M $HNO_3$ with stirring at 60° C. The stirring solution was cooled to room temperature and the silane mixture was added drop-wise. The reaction mixture was stirred until homogeneous and transferred to a culture tube which was sealed tightly and heated at 60° C. overnight (~18 h). The tube was unsealed and the white gel was heated at 60° C. for 2 d and then 80° C. for 2 d. P123 was extracted by refluxing the monolith three times in ethanol for at least 12 h. A powdered product was collected by suction filtration, rinsed with ethanol and water, and dried at 100° C. For MM5, 0.3 g TMB was used with 6 g 0.1 M $HNO_3$. The total mol Si used was 7.84 mmol with 50:50 BTE:DEB. In the case of P10 and P5, 0.55 g TMB was used with 7.5 g 0.1 M $HNO_3$. The silane mixture consisted of 15.7 mmol total Si with either 50:40:10 (P10) or 50:45:5 (P5) BTE:DEB:PTS.

For N5, the protocol utilized 0.3 g TMB with 9.5 g 0.1 M $HNO_3$ and the silane mixture was 100% BTE.[49] Following synthesis, amine groups were grafted on to the materials by adding sorbent (1 g) to 200 mL of toluene with 1 g 3-aminopropyltrimethoxysilane (APS).[65] Alternatively, the amine groups can be incorporated during synthesis instead of by grafting, via substitution of APS for part (typically 12% or less) of the BTE precursor. This mixture was refluxed for 24 h after which the grafted product was collected by vacuum filtration, washed with toluene then ethanol, and dried at 110° C. The DEN sorbent is a variation of this material. Following the amine functionalization protocol, isocyanate groups were incorporated using the ICS precursor.[65] This sorbent (1 g) was then placed in 50 mL MES buffer (100 mM, pH 5.5) with 1.3 g polyamidoamine (PAMAM) dendrimer (10 wt. % in methanol) and mixed on a rotisserie mixer overnight at room temperature. The sorbent was collected by vacuum filtration, washed with methanol, and dried at 110° C.

N5 was a mesoporous ethane-bridged silica with some amine functionalities incorporated in its structure by addition of 3-aminopropyltrimethoxysilane. It featured a large mesopore size ca. 77 Å and high surface area and pore volume values of 1,000 $m^2/g$ and 1.19 $cm^3/g$, respectively. The symmetry of its type IV nitrogen sorption isotherm with parallel adsorption and desorption branches, along with its sharp pore size distribution, indicated regularity in the mesostructure, though not necessarily long-range crystalline-like order. N5 was synthesized as a monolith. Surfactant extraction by reflux resulted in crushing of this monolith to a powder with granule sizes on the order of hundreds of microns.

Sorbents with Alkylammonium Groups. The alkylammonium-group-bearing sorbents (HX, CF prefixes) were synthesized based on a published approach.[66-68] For synthesis of the HX sorbent, 4.0 g of Pluronic P123 and 0.85 g of TMB were dissolved in 12.0 g of 1.0 M HNO3 with magnetic stirring and heating at 60° C. The stirring mixture was allowed to cool to room temperature and 5.15 g of TMOS was added drop-wise. The mixture was stirred until homogeneous, transferred to a culture tube, sealed tightly, and heated at 60° C. overnight (≥18 h). The white monolith was dried in the unsealed tube at 60° C. for approximately 5 days before calcination (ambient atmosphere, temperature ramped 1° C./min to 650° C. and held for 5 h) to remove surfactant. The CF sorbent was synthesized identically with the exception of the TMB included which was 3.10 g. Materials were dried at 110° C. prior to grafting with alkylammonium silanes which was accomplished by adding sorbent (1 g) to 100 mL of toluene followed by addition of 2 mmol of both TSPMC and TSPBC to produce the HX2M2B and CF2M2B sorbents. This mixture was refluxed for 24 h after which the grafted product was collected by vacuum filtration, washed with toluene then ethanol, and dried at 110° C. An additional sorbent, CF1 was synthesized identically with the exception of the TSPMC and TSPBC used, 0.5 mmol of each in this case.

CF1 was further functionalized using approaches previously described to produce multifunctional materials. CF-BT was synthesized by incubating CF1 (100 mg) with 50 mg trehalose and 100 mg BSA in water (15 mL) for 3 h. Following incubation with agitation, the materials were centrifuged and rinsed to remove excess sugar and protein, and they were dried at 110° C. CF-B was synthesized by incubation of CF1 (100 mg) with APS (0.3 mmol) in toluene (10 mL) for 45 min. After rinsing, the APS modified material was incubated with BSA (100 mg) in a solution of 5 mM EDC in 100 mM MES buffer pH 5.5. CF-T was synthesized by incubation of CF1 (100 mg) with ICS (0.3 mmol) in toluene (10 mL) for 45 min. After rinsing, the ICS modified material was incubated with trehalose (100 mg) in PBS. For synthesis of CF-2X, CF1 (100 mg) was incubated with ICS (0.15 mmol) and APS (0.15 mmol) in toluene (10 mL) for 45 min. After rinsing, the APS/ICS modified material was incubated with trehalose (50 mg) and BSA (50 mg) in a solution of 5 mM EDC in 100 mM MES buffer pH 5.5.

Metal Functionalized Sorbents.

Metal-functionalized sorbents (CuEDA, ZnEDA) utilized N-(-2-aminoethyl)-3-aminopropyltrimethoxysilane (EDA) for chelation. Synthesis used an adapted protocol[69-71] in which BTE (3.2 g) was dissolved in 0.01 M HCl (4 g). P123 (0.65 g) was added to the mixture and allowed to fully dissolve. The metal chelating group, EDA (0.11 g) was then added with either zinc chloride (0.04 g) or copper chloride (0.04 g) and a vacuum was pulled on the solutions for 24 h. Other metal salts could be used to incorporate the copper or zinc. The tube was sealed and placed in an oven at 100° C. for 0.5 h followed by 60° C. for 24 h. Sorbents were refluxed twice in acidified ethanol to remove the surfactant and soaked overnight in an ammonium hydroxide solution. After rinsing, metals were reincorporated through refluxing in a 0.1 M solution of either copper chloride or zinc acetate.

CuEDA was a mesoporous ethane-bridged silica with pendant ethylenediamine (EDA) functionalities resulting from addition of N-(2-aminoethyl)-3-aminopropyltrimethoxysilane. EDA groups were included to chelate $Cu^{2+}$ metal ion. The material exhibited a type IV nitrogen sorption isotherm with high respective surface area and pore volume values of 716 $m^2/g$ and 0.87 $cm^3/g$ and a uniform pore size distribution centered at 64 Å.

CuEDA was synthesized as a monolith. Surfactant extraction by reflux resulted in crushing of this monolith to a powder with granule sizes on the order of hundreds of microns.

Chitosan Sorbents.

The reactor for this synthesis consisted of a 1000 mL PTFE jar set in a water bath maintained at 80° C. Cetyltrimethylammonium bromide (1.0 g) and 1.0 N NaOH (6.0 mL) were dissolved in 475 mL of $H_2O$ with magnetic stirring.[53,62] Mesitylene (6.0 mL) was added, and the solution was stirred for 3 h. Tetraethyl orthosilicate (TEOS; 5 mL) was added, and the mixture was stirred; white precipitate formed quickly. After 2 h, the precipitate was collected on filter paper by gravity filtration. When dry, the material was refluxed in 160 mL of ethanol with 9 mL of hydrochloric acid (37%) for 1 d to extract surfactant. The extracted product was collected by centrifugation, and washed with ethanol followed by water (3 times). The sorbent was dried at 110° C. prior to functionalization. To incorporate chitosan, a mixture of 1 g chitosan and 100 mL of 1 vol % acetic acid was prepared and filtered to remove insoluble matter. The sorbent was magnetically stirred in 50 mL of chitosan solution at room temperature for 1 d. The functionalized material (ChTS) was collected by centrifugation and washed with $H_2O$ three times before drying at 70° C.

For a different approach to development of a chitosan-functionalized sorbent (ChMS), a (3-glycidoxypropyl) trimethoxysilane-functionalized material was synthesized for covalent anchoring of chitosan by adapting a published procedure [J. Kobler, K. Möller, and T. Bein, "Colloidal Suspensions of Functionalized Mesoporous Silica Nanoparticles," *ACS Nano* 2, 791-799 (2008)]. Cetyltrimethylammonium chloride reagent (2.67 g; 25% in $H_2O$) was diluted with 24 g of $H_2O$ in a 60 mL Teflon jar and heated in an oven at 60° C. In a separate 120 mL Teflon jar, a two-phase mixture was made of 14.3 g triethanolamine with 2.083 g tetraethyl orthosilicate and 0.48 g (3-glycidoxypropyl) trimethoxysilane; the mixture was heated at 90° C. in an oven for at least 20 min. The two heated mixtures were removed from the ovens and combined immediately; the combined mixture was stirred at 600 RPM for 3 h (RT). Ethanol (50 mL) was added and the precipitate was collected by centrifugation. The solid was washed with ethanol and centrifuged. The precipitate was dried at 60° C. Cetyltrimethylammonium chloride surfactant was ion-exchanged by dispersing the material in 50 mL $NH_4NO_3$ ethanol solution (20 g/L), stirring and heating at 60° C. overnight. The material was collected by centrifugation and washed with ethanol. After drying the material at 80° C., the ion-exchange process was repeated two more times with fresh $NH_4NO_3$ solution. The material was washed with ethanol, centrifuged, and washed with $H_2O$. A second ion-exchange was performed by stirring the material in 50 mL HCl/ethanol solution (5 g/L concentration) at RT for 1 d. Material was collected by centrifugation, washed once with ethanol and twice with $H_2O$. The product was dried first at 60° C. in centrifuge tubes that were lightly capped overnight, then uncapped and dried thoroughly at 80° C. A 2 wt % chitosan oligosaccharide lactate solution was prepared in 1 wt % acetic acid. The silicate material was stirred in 50 g of chitosan oligosaccharide lactate solution at 60° C. for 1 d. Material was collected by centrifugation, washed 4 times with $H_2O$, and dried at 60° C.

A sorbent might be associated with one or more stabilizers such as BSA, trehalose, and/or glucosamine.

Sorbent Characteristics

The chemical composition of the sorbents considered covers a wide range of possible activities (FIG. 1). Diethylbenzene-bridged materials and those functionalized with pendent phenyl groups offer a somewhat hydrophobic environment as well as a high concentration of π-bonds (MM5, P5, P10). The hydroxyl groups of these types of silicate materials tend to be acidic; incorporation of primary amine groups offers basic sites (N5). The dendrimer modification (DEN) provides a greater number of basic sites at greater distance from the surface and increased hydrophobicity in the sorbent. The alkylammonium functionalities offer cationic groups in two different material morphologies with relatively disordered (CF2M2B) and ordered (HX2M2B) mesopore structures. Chitosan (ChTS) offers antimicrobial activity as well as the potential for multiple and complex cationic interactions with nucleic acids. The materials with ethylenediamine pendent groups (CuEDA and ZnEDA) offer sites for metal ion chelation. The presence of cations is known to impact the secondary structure of DNA; the presence of copper has been shown to decrease DNA melting temperatures while zinc causes an increase.

The below Table 1 provides a summary of the materials utilized and their morphological characteristics.

TABLE 1

Material Characteristics.

| Material | Description | S. Area ($m^2/g$) | Pore Vol ($cm^3/g$) | Pore Dia (Å) |
|---|---|---|---|---|
| NS* | Bare silicate sorbent; no organic groups | 730 | 0.75 | 50 |
| N5 | Primary amine groups on BTE sorbent | 1002 | 1.19 | 77 |
| P5 | Phenyl groups on DEB sorbent | 470 | 0.46 | 50 |
| P10 | Phenyl groups on DEB sorbent | 440 | 0.43 | 43 |
| MM5 | DEB sorbent | 606 | 0.51 | 44 |
| CuEDA | Coordinated copper on BTE sorbent | 716 | 0.87 | 64 |
| ZnEDA | Coordinated zinc on BTE sorbent | 275 | 0.70 | 223 |
| HX2M2B | Alkylammonium groups on ordered pore structure (TMOS) | 169 | 0.26 | 63 |
| CF2M2B | Alkylammonium groups on mesostructure cellular foam (TMOS) | 143 | 0.18 | 93 |
| DEN | Amine and C12 terminated dendrimer on BTE sorbent | 649 | 0.75 | 40 |
| ChTS | Chitosan on TEOS | 550 | 0.82 | 54 |

The materials were screened by generating a data set consisting of binding data for RNA and DNA using two target concentrations (FIG. 2A). The goal was to identify the types of functional characteristics that provided significant adsorption of the two targets, so that those materials could be evaluated fully. The results of this screening were unexpected; some materials bound high percentages of the DNA or RNA while binding little to none of the other target. Similar data for the binding of ssDNA was collected to determine if the single versus double stranded nature of the targets was a significant contributor to these differences and to provide an additional point of comparison between the materials. The results of ssDNA binding were consistent with neither the DNA nor RNA binding (FIG. 2A) indicating that the single or double stranded nature of the targets was not the primary contribution to the difference in binding efficiency of the materials.

The Langmuir-Freundlich (LF) binding isotherm is a generalized form of the Langmuir model often applied to solid sorbents. This isotherm was applied to the data sets generated for target binding. Parameters were generated for each of the materials: an effective affinity constant for the target (k), the saturated loading capacity of the sorbent ($q_s$), and the site heterogeneity (n) within the sorbent based on the free ([L], ng) and bound target (q, ng/μg). Here, the constant α divided by the mass (m) yields the more typically utilized saturation capacity ($q_s$) for the model.[73-75]

$$q = \frac{\frac{\alpha}{m}k[L]^n}{1+k[L]^n} \quad \text{(Eq. 1)}$$

Figure 3A:
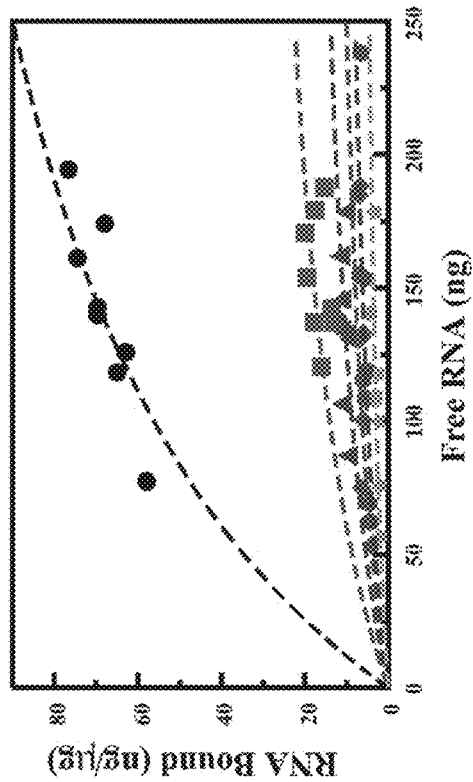
FIGS. 3A and 3B show binding isotherms. RNA bound by the N5 sorbent without pre-washing (a) and following the described wash step (b). Here, sorbent masses of 2 (black circle), 8 (red square), 13 (blue triangle), 18 (green diamond), 23 (purple hexagon), and 40 μg (orange star) were utilized for capture of RNA from a 240 μl solution containing ~300 ng RNA target.

In order to better understand the interactions between the NA targets and the sorbents, isotherms for each of the materials with each of the three targets were generated. Table 2 provides a summary of the resulting parameters and fit statistics. In the case of these materials, site heterogeneity was found to be one (n=1) for all targets. FIG. 3A presents data from RNA adsorption experiments and the calculated binding isotherms for N5.

RNA concentrations, N5 will bind more target than HX2M2B (k=0.0467 $ng^{-1}$ versus 0.00818 $ng^{-1}$). N5 provided the greatest DNA saturated loading limit, while HX2M2B provided the greatest limit for ssDNA. MM5, P5, and P10 showed moderate to low total binding and affinity for all three targets. DEN performed moderately for RNA and ssDNA and bound by far the greatest amount of DNA. CuEDA and ZnEDA performed moderately for DNA and ssDNA, but CuEDA provided the greatest RNA saturated loading limit.

Elution of bound target from the sorbent materials was also evaluated. Initial attempts at recovering RNA using EB buffer (10 mM Tris-Cl, pH 8.5) at 50° C. (total volume 20 μL) provided minimal return from these materials. Although NEB buffer (20 mM Tris-Cl, pH7.5, 1 mM EDTA) provided the best performance in a previous study[62], but did not offer target recovery from these materials. Variations on temperature, volume, incubation period, and detergent concentrations were considered and tested as was the inclusion of solvent and sodium chloride. Other studies have indicated the impact of buffer pH on the elution efficiency related to silicate materials; however, varying pH (5.7 to 8.0) did not have an impact on RNA recovery. It has been argued that nucleic acid interactions with silicate materials are via amine and carboxyl groups. Methods used to displace these interactions as well as those used to displace RNA from negatively charged membranes were considered and tested with-

TABLE 2

Langmuir isotherm parameters for RNA, DNA, and ssDNA binding by unwashed sorbents.

| | RNA | | | | DNA | | | | ssDNA | | | |
|---|---|---|---|---|---|---|---|---|---|---|---|---|
| Material | α (ng/μg · μg) | k ($ng^{-1}$) × $10^{-3}$ | $Chi^2$ | St. Error | α (ng/μg · μg) | k ($ng^{-1}$) × $10^{-3}$ | $Chi^2$ | St. Error | α (ng/μg · μg) | k ($ng^{-1}$) × $10^{-3}$ | $Chi^2$ | St. Error |
| | | | | | Unwashed Sorbents | | | | | | | |
| NS* | 410 | 550 | — | — | 1530 | 38.3 | 105 | 4.81 | 75.7 | 4.72 | 136 | 1.39 |
| N5 | 165 | 46.7 | 381 | 3.45 | 9.14 | 0.661 | 187 | 6.34 | 62.6 | 0.512 | 25.7 | 0.607 |
| P5 | 204 | 6.91 | 691 | 3.91 | 9.26 | 0.698 | 561 | 9.71 | 38.2 | 0.478 | 45.9 | 0.810 |
| P10 | 104 | 7.92 | 552 | 3.50 | 118 | 8.53 | 852 | 4.33 | 147 | 1.12 | 407 | 2.41 |
| CuEDA | 690 | 6.03 | 2920 | 7.09 | 55.8 | 4.14 | 422 | 10.5 | 104 | 0.707 | 75.4 | 1.14 |
| ZnEDA | 301 | 1.95 | 234 | 2.26 | 9.13 | 0.614 | 110 | 1.33 | 57.6 | 177 | 200 | 2.08 |
| MM5 | 97.6 | 17.7 | 200 | 2.08 | 114 | 8.27 | 60.3 | 3.62 | 256 | 1.78 | 327 | 2.67 |
| HX2M2B | 375 | 8.18 | 1421 | 4.95 | 26.2 | 1.91 | 118 | 1.60 | 158 | 1.06 | 141 | 1.83 |
| CF2M2B | 571 | 9.18 | 3580 | 8.83 | N/A† | N/A | N/A | N/A | 94.8 | 0.563 | 634 | 3.71 |
| DEN | 279 | 31.8 | 960 | 5.73 | N/A† | N/A | N/A | N/A | 7.43 | 0.467 | 5.64 | 0.284 |
| ChTS | 255 | 42.9 | 1520 | 5.75 | | | | | | | | |
| | | | | | Washed Sorbents | | | | | | | |
| N5 | 300 | 6.13 | 124 | 1.64 | 61.4 | 4.48 | 1315 | 8.48 | 157 | 1.10 | 41.7 | 0.952 |
| CuEDA | 167 | 30.2 | 924 | 3.60 | 60.6 | 4.41 | 905 | 6.17 | N/A† | N/A | N/A | N/A |
| HX2M2B | 220 | 82.1 | 247 | 2.06 | 8.78 | 0563 | 344 | 11.1 | 113 | 0.728 | 16.4 | 0.604 |
| DEN | 165 | 202 | 1260 | 3.35 | 184 | 13.3 | 213 | 6.81 | 176 | 1.22 | 90.4 | 1.43 |

*NS is the base sorbent from previous work.[62]
†Insufficient data for generation of an isotherm;
DEN ~100% bound,
ChTS ~0% bound,
CuEDA ~0% bound The parameters obtained indicate the maximum target that can be bound (α) and the rate at which that limit will be approached (k). For example, the RNA saturated loading limit for HX2M2B is greater than that of N5, but, at low free out improvement. Finally, various nucleic acid washing solutions and hybridization buffers were evaluated without success (less than 1% of target recovered). The solutions and condition variations evaluated are summarized in Table 3.

TABLE 3

Elution solutions and conditions evaluated.

| Solution | Volume (μL) | Time (h) | Temperature (° C.) |
|---|---|---|---|
| EB buffer (10 mM Tris-Cl, pH 8.5) | 20, 50, 200 | 0.3, 3 | 50 |
| EB buffer (10 mM Tris-Cl, pH 8.5) with 0.1% Tween 20 | 50 | 0.3 | 50 |
| EB buffer (10 mM Tris-Cl, pH 8.5) with 0.1% SDS | 50 | 03 | 50 |
| EB buffer (10 mM Tris-Cl, pH 8.5) with 0.1% SDS and Tween20 | 50 | 0.3 | 50 |
| Nuclease-free water | 20, 50, 200 | 0.3, 3 | RT, 65, 95 |
| 1x GoTaq PCR buffer (Promega) with 0.1% SDS | 20, 100, 200 | 0.3, 3 | 50 |
| NEB buffer | 50 | 0.3 | 50 |
| NEB buffer with 0.1% SDS | 50, 100 | 0.3 | 50 |
| 50 mM sodium phosphate buffer pH 5.7 to 8.0 | 50 | 0.3, 5 | 50 |
| 50 mM sodium phosphate buffer with 0.1% Tween 20, pH 7.2 | 50 | 0.3 | 50 |
| 10, 50, 100, 200, or 250 mM Tris pH 8.0 | 50, 100, 200 | 0.3 | 50 |
| 10, 100, or 200 mM Tris with 20% ethanol | 100 | 0.3 | 50 |
| 10 mM Tris with 50, 100, 150, or 200 mM NaCl pH 8.0 | 50, 100, 200 | 0.3 | 50 |
| 10 mM Tris with 1, 5, or 10% Triton X100 pH 8.0 | 50 | 0.3 | 50 |
| 10 mM Tris with 100 mM NaCl and 0.1% SDS | 100 | 0.3 | 50 |
| 10 mM Tris with 100 mM NaCl and 1% Triton X-100 | 100 | 0.3 | 50 |
| 25 mM Tris with 250 mM Glycine pH 8.0 or 7.0 | 100 | 0.3 | 50 |
| 25 mM Tris with 250 mM Glycine & 0.1% SDS pH 8.0 or 7.0 | 100 | 0.3 | 50 |
| 25 mM Tris with 250 mM Glycine & 1% Triton X-100 | 100 | 0.3 | 50 |
| 100 mM Tris with 50 mM Glycine pH 8.0 or pH 9.5 | 100 | 0.3 | 50 |
| 100 mM Tris with 50 mM Glycine and 0.1% SDS pH 9.5 | 100 | 0.3 | 50 |
| 100 mM Tris with 50 mM Glycine and 1% Triton X-100 pH 8.0 | 100 | 0.3 | 50 |
| 100 or 200 mM Tris with 0.1% SDS pH 8.0 | 100 | 0.3 | 50 |
| 200 mM Tris with 50 or 100 mM NaCl pH 8.0 | 50, 100 | 0.3 | 50 |
| 200 mM Tris with 100 mM NaCl and 20% ethanol, pH 8.0 | 100 | 0.3 | 50 |
| 200 mM Tris with 0.1% SDS and 20% ethanol, pH 8.0 | 100 | 0.3 | 50 |
| 200 mM Tris with 0.1% SDS, pH 8.0 | 100 | 0.3 | 50 |
| Hyb buffer (MiSeq) | 100 | 0.3 | 50 |
| Hyb buffer (Affymetrix) | 100 | 0.3 | 50 |
| 0.2X or 2X SSC with 0.1% SDS | 100 | 0.3 | 50 |
| 0.6X or 6X SSPE with 0.1% SDS | 100 | 0.3 | 50 |
| 0.31, 0.63, 1.3, or 2.5M NaCl | 100 | 0.3 | 50 |
| 50 mM Glycine with 150 mM NaCl pH 9.5 | 100 | 0.3 | 50 |
| 50 mM Glycine with 150 mM NaCl and 0.1% SDS pH 9.5 | 100 | 0.3 | 50 |
| 1xTAE with 0.1% SDS | 100 | 0.3 | 50 |
| Washed Sorbents | | | |
| 10 mM Tris pH 8.0 | 100 | 0.3 | 50 |
| 10 mM Tris with 20% ethanol | 100 | 0.3 | 50 |
| 100 mM Tris with 0.1% SDS | 100 | 0.3 | 50 |
| 10 mM Tris with 100 mM NaCl | 100 | 0.3 | 50 |
| NEB with 0.1% SDS | 100 | 0.3 | 50 |
| Washed DEN Sorbent | | | |
| 1x PCR 0.1% SDS NEB with 0.1% SDS | 100 | 0.3 | 50 |
| 10 mM Tris pH 8.0 | 100 | 0.3 | 50 |
| 10 mM Tris with 20% ethanol | 100 | 0.3 | 50 |
| 10 mM Tris with 100 mM NaCl | 100 | 0.3 | 50 |
| 10 mM Tris with 100 mM NaCl and 0.1% SDS | 100 | 0.3 | 50 |
| 10 mM Tris with 100 mM NaCl and 1% Triton X-100 | 100 | 0.3 | 50 |
| 25 mM Tris with 250 mM Glycine and 0.1% SDS | 100 | 0.3 | 50 |

TABLE 3-continued

Elution solutions and conditions evaluated.

| Solution | Volume (μL) | Time (h) | Temperature (° C.) |
|---|---|---|---|
| 25 mM Tris with 250 mM Glycine and 1% Triton X-100 | 100 | 0.3 | 50 |
| 100 mM Tris with 0.1% SDS | 100 | 0.3 | 50 |
| 100 mM Tris with 50 mM Glycine and 0.1% SDS | 100 | 0.3 | 50 |
| 100 mM Tris with 50 mM Glycine and 1% Triton X-100 | 100 | 0.3 | 50 |
| 0.6X SSPE with 0.1% SDS | 100 | 0.3 | 50 |
| 0.6X SSPE with 1% Triton X-100 | 100 | 0.3 | 50 |

Figure 3B:
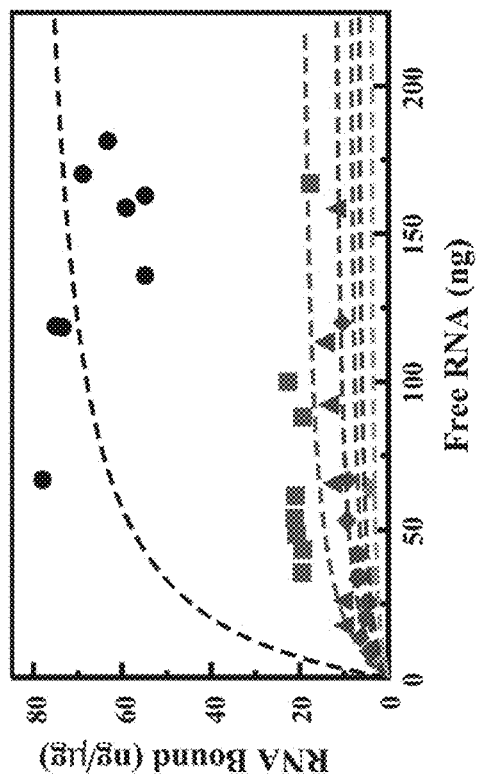

Given the failure of this wide range of elution solutions, the possibility that the nucleic acids were destroyed on interaction with the sorbents was considered; however, given previous work in this area and the wide range of sorbent variations involved, these types of destructive interactions are unlikely to be observed for all of the materials under consideration. Based on previous experience and other materials used for nucleic acid hybridization, a pre-wash step was evaluated for the sorbents. Here, the procedure involved incubating the sorbent in 10 mM Tris with 1% Triton X-100 for 15 min at room temperature prior to NA adsorption. FIG. 2B provides single point data on target binding by the washed N5, CuEDA, HX2M2B, CF2M2B, DEN and ChTS. Other sorbents considered for this study bound less than 5% of all three targets. This pre-conditioning step strongly impacted the binding behavior of the sorbents and led to less error in the resulting fits (Table 2; FIG. 3B). ZnEDA offered lower saturated loading capacities than CuEDA prior to washing and likely lost binding capacity upon interaction with the Triton X-100 as observed for CuEDA. This surfactant would also be expected to interact with the surfaces of the MM5, P5, and P10 sorbents given their somewhat hydrophobic nature and the available π-interaction sites.

FIGS. 2A and 2B show results of binding assays. Without a pre-wash step, the results of ssDNA binding were consistent with neither the DNA nor RNA binding (FIG. 2A) indicating that the single or double stranded nature of the targets was not the primary contribution to the difference in binding efficiency of the materials. FIG. 2B provides single point data on target binding by the washed N5, CuEDA, HX2M2B, CF2M2B, DEN and ChTS. Other sorbents considered for this study bound less than 5% of all three targets. This pre-conditioning step strongly impacted the binding behavior of the sorbents and led to less error in the resulting fits (Table 2; FIG. 3B).

Alternative pre-wash solutions, such as 2×SSC (0.3 M sodium chloride with 30 mM trisodium citrate at pH 7) with 0.1% SDS or 6×SSPE (900 mM NaCl with 60 mM sodium phosphate and 6 mM ethylenediaminetetraacetic acid) with 0.1% SDS, could be considered for use with these sorbents. It is expected that other pre-wash solutions including a detergent and optionally a buffer would also operate to effectively pre-condition the sorbents to improve the ability to recover targets by elution.

Figures 4A, 4B, 4C:
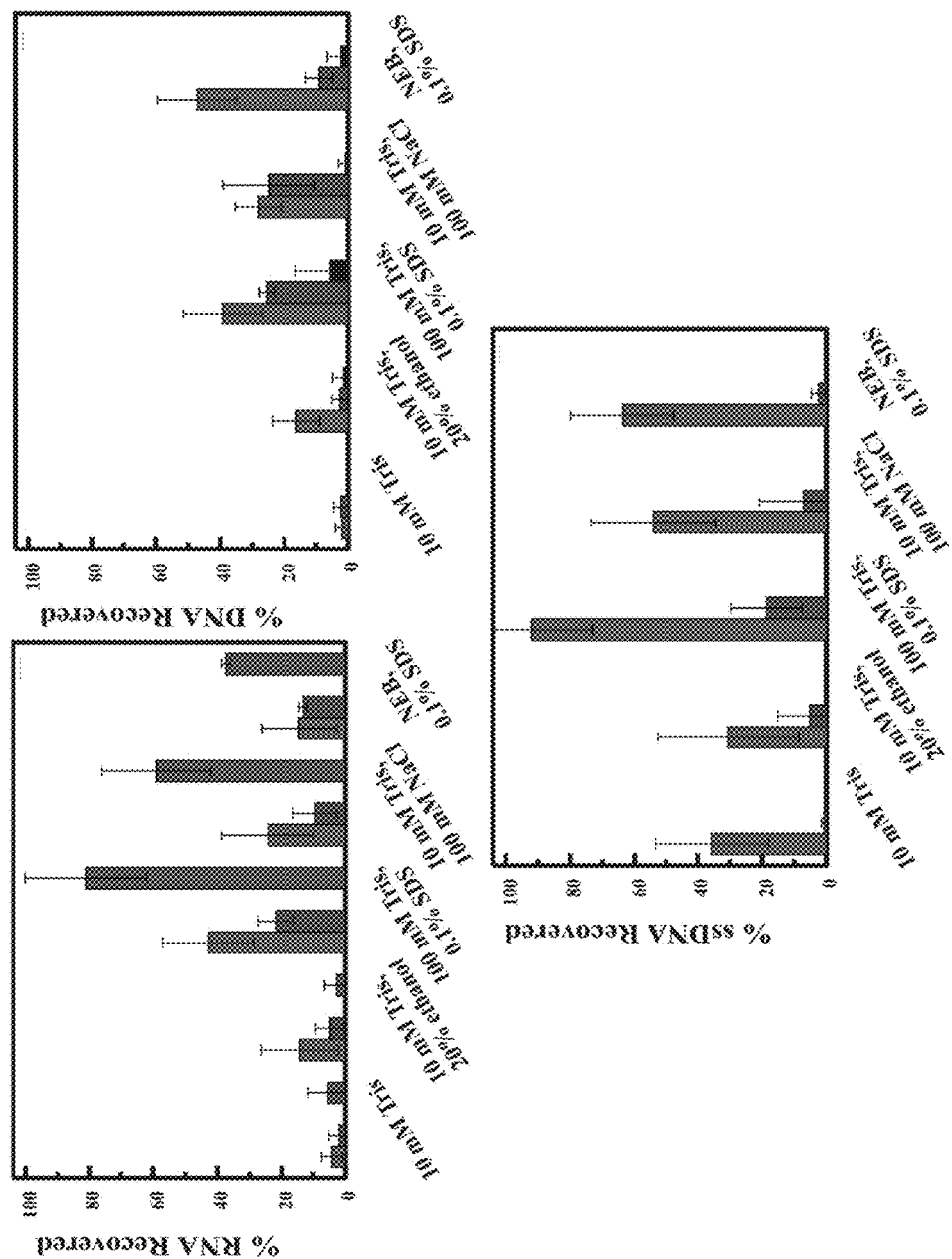
FIGS. 4A, 4B, and 4C show RNA recovery by elution. RNA eluted from washed sorbent materials reported as a percentage of the target initially adsorbed: N5 (red); HX2M2B (blue); DEN (black); CuEDA (green). All elution solutions utilized 100 μL at 50° C. for 20 min: RNA (a), DNA (b), and ssDNA (c).

The potential for elution of targets was evaluated using the pre-conditioned materials, and variations on the elution solution were again considered. FIGS. 3A and 3B show binding isotherms with and without the wash step. RNA recovery was significantly increased from less than 1% in the unwashed sorbents to between 20 and 80% using 100 mM Tris with 0.1% SDS for HX2M2B, N5, and CuEDA. Recovery of DNA and ssDNA was also improved following the pre-conditioning step with a small amount of DNA recovered from even the DEN sorbent. FIGS. 4A-4C show elution recovery percentages of nucleic acids from various sorbents.

Figures 5A, 5B, 5C:
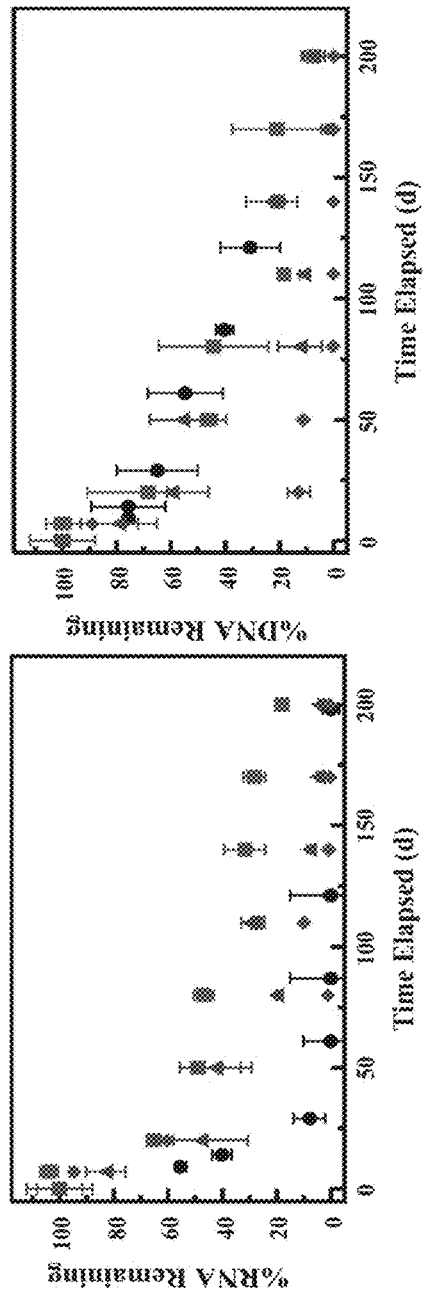
FIGS. 5A, 5B, and 5C show stability of NA targets. NA targets recovered from N5 (red square), HX2M2B (blue triangle), and DEN (green diamond) following storage at room temperature. Data for similarly stored target only in solution (circle) is provided for comparison: RNA (a), DNA (b), and ssDNA (c).
Figure 6A:
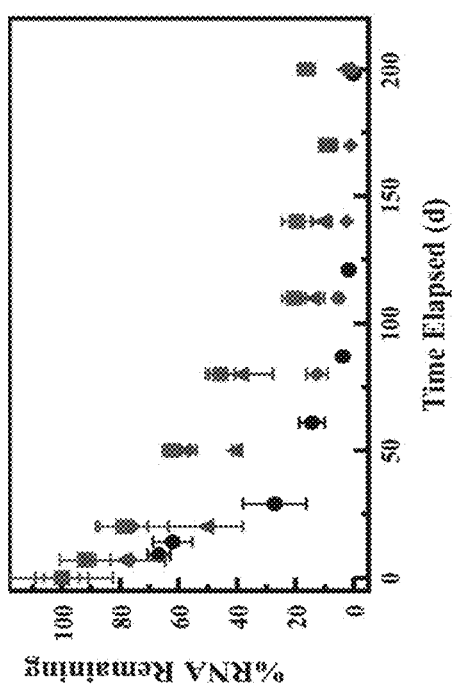
FIGS. 6A, 6B, and 6C show of NA targets at 37° C. NA targets recovered from N5 (red square), HX2M2B (blue triangle), and DEN (green diamond) following storage at 37° C. Data for similarly stored target only in solution (circle) is provided for comparison: RNA (a), DNA (b), and ssDNA (c).

In order to evaluate the potential of the sorbents in enhancement of the stability of stored NA targets, a large batch sample for each material in each target was prepared. The sample was then divided into aliquots, the supernatants were separated from the precipitated sorbents, and the sorbents were left to dry at room temperature overnight. A control sample consisting of the target only in solution was retained for comparison. The sorbents were sampled following storage either at room temperature or at 37° C. No special protection from light or control of humidity was employed. Storage at 37° C. is intended to simulate temperatures relevant to those expected at the high end of operational conditions. Over the course of the experiments, room temperature varied between 18 and 23° C. while relative humidity ranged from 42 to 61%. FIG. 5A presents the results of RNA storage over a period of 200 days at room temperature. The recovered RNA is normalized to the amount recovered on day one of the experiment. Over this period, RNA eluted from N5 gradually decreases to 20% of the day one recovery while that from HX2M2B decreases to 5%. Recovery from DEN, significantly lower on day one, decreases to <10% by day 80. RNA in the control sample drops to <10% by day 29. At 37° C., recovery of RNA from all three materials was increased as compared to that from the control sample (FIG. 6A). More than 20% was recovered from N5 through day 140, from HX2M2B through day 80, and from DEN through day 50. These results indicate that the three sorbents offer improvements in RNA stability both at room temperature and at 37° C.

Figure 6B:
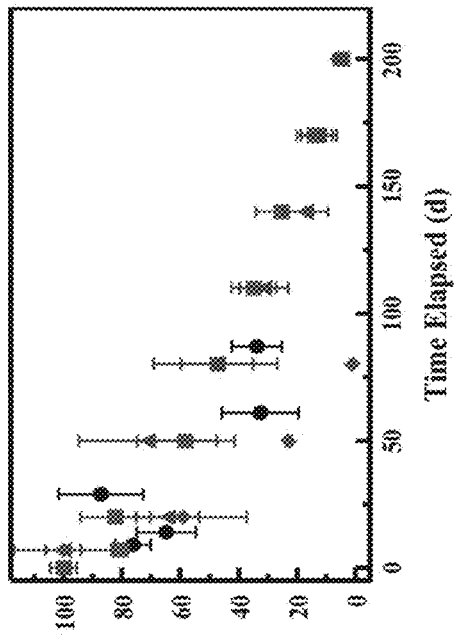
Figure 6C:
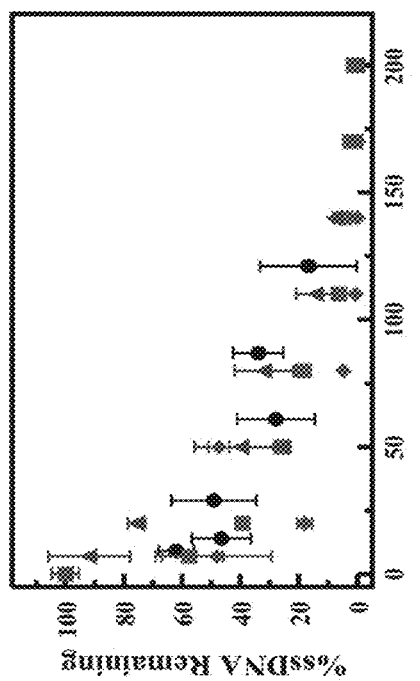

The decrease in DNA recovered from N5 and HX2M2B at room temperature and at 37° C. was similar to the decrease in the DNA content of the control sample (FIG. 5B and FIG. 6B). For ssDNA, on the other hand, while the control sample at room temperature dropped below 20% of the original content on day 121, recovery from N5 remained above 20% beyond day 170. When stored at 37° C., however, the decrease in ssDNA recovered from N5 was similar to that of the control sample. While the decrease in ssDNA recovered from HX2M2B at room temperature was similar to the decrease in the ssDNA content of the control sample, HX2M2B showed slightly improved recovery of ssDNA over the first 20 days at 37° C. Results with DEN showed more rapidly decreasing DNA and ssDNA content than that observed for the control samples.

Binding from Complex Solutions

In practice, it can be desirable for a sorbent to bind nucleic acids directly from a complex solution that can include proteins, carbohydrates, lipids, and/or other materials. For example, lysis of cells to obtain nucleic acids will result in a complex mixture. One might wish to avoid purifications steps to the extent possible.

*Escherichia coli* was used to prepare samples for evaluation of target binding from complex solution. *E. coli* was streaked from glycerol stock onto LB agar plate and incubated overnight at 37° C. A single colony was picked from the plate and grown in 5 mL LB broth overnight at 37° C.; this was used to inoculate 50 mL LB broth. $OD_{600}$ was measure every hour after inoculation, and 1.5 mL of cells were aliquoted into 1.5 mL Eppendorf tubes and stored at 4° C. until ready to use. Bacteria cells were pelleted by centrifuge at 5,000 g for 10 min; supernatant was discarded; and pellets were subjected to various lysis conditions. Genomic DNA was extracted from a sample using MasterPure™ Complete DNA and RNA Purification Kit (Epicentre) for use as a control and for generation of a standard curve. Several lysis buffer/conditions were identified based on published protocols:

1. Bacteria was resuspended in Tris-EDTA buffer (100 μL; 30 mM Tris, pH 8.0 and 1 mM EDTA) with 5 mg/mL lysozyme and 1 μL proteinase K. The mixture was incubated at room temperature for 10 min. A microcentrifuge was used to spin down cell debris (maximum speed for 2 min). The supernatant containing genomic DNA was transfer to a new Eppendorf tube for OD and qPCR assessment.

2. Similar to protocol of 1 without proteinase K.

3. Same composition as 1. Following incubation, Buffer RLT was added to the mixture prior to centrifugation.

4. Same composition as 1. Following incubation, cells were subjected to three freeze and thaw cycles prior to centrifugation.

5. Similar to protocol of 4 without proteinase K.

6. Bacteria was resuspended in Tris-NaCl buffer (100 μL; 50 mM Tris, pH 8.0 and 150 mM NaCl) with 0.4 mg/mL lysozyme. The mixture was subjected to three freeze and thaw cycles A microcentrifuge was used to spin down cell debris (maximum speed for 10 min). The supernatant containing genomic DNA was transferred to a new Eppendorf tube for O.D. and qPCR assessment.

7. Similar to 6 without lysozyme in the buffer.

8. Bacteria was resuspended at 100 μL of Tris-Triton (100 mM Tris, pH 8.0 and 2% Triton X-100) buffer with 10 mg/mL lysozyme. The mixture was incubated at room temperature for 10 minutes. A microcentrifuge was used to spin down cell debris (maximum speed for 2 min). The supernatant containing genomic DNA was transferred to a new Eppendorf tube for OD and qPCR assessment.

9. Similar to protocol of 8 without lysozyme in the buffer.

10. Bacteria was resuspended in PBS/EDTA/Triton buffer (100 μL; 0.5×PBS, 1 mM EDTA, 0.1% Triton X-100) with 10 mg/mL lysozyme. The mixture was subjected to three freeze and thaw cycles. A microcentrifuge was used to spin down cell debris (maximum speed for 10 min). The supernatant containing genomic DNA was transferred to a new Eppendorf tube for OD and qPCR assessment.

11. Similar to protocol of 10 with no lysozyme in the buffer.

12. Bacteria was resuspended in buffer P1 (Qiagen; 50 μL) and mixed with buffer P2 (Qiagen; 50 μL). Buffer N3 (Qiagen; 70 μL) was added and the solution was inverted to mix. A microcentrifuge was used to spin down cell debris (maximum speed for 10 min). The supernatant containing genomic DNA was transferred to a new Eppendorf tube for OD and qPCR assessment.

13. Bacteria was resuspended in Tris-sucrose (50 μL; 25 mM Tris, pH8.0 and 20% w/v sucrose) with 20 mg/mL lysozyme (5 μL) and incubated on ice for 5 mins. EDTA (5 μL; 0.5 M) was added followed by lysis buffer (50 μL; 50 mM Tris, pH 8.0 and 25 mM EDTA, 2% Triton X-100). The solution was incubated at room temperature for 15 min. A microcentrifuge was used to spin down cell debris (maximum speed for 10 min). The supernatant containing genomic DNA was transferred to a new Eppendorf tube for OD and qPCR assessment.

DNA concentrations were measured using Nanodrop 2000 (Thermo Scientific) to assess the 260/280 ratios. A stock solution (40 ng/μL) was prepared based on the OD reading and used for qPCR assessment. qPCR was performed using primers designed to target DNA polymerase III delta prime subunit (HolB) of *E. coli*. Based on OD readings and qPCR results, the PBS/EDTA/Triton buffer was selected for testing the performance of sorbents for adsorption and elution of targets.

Figure 7B:
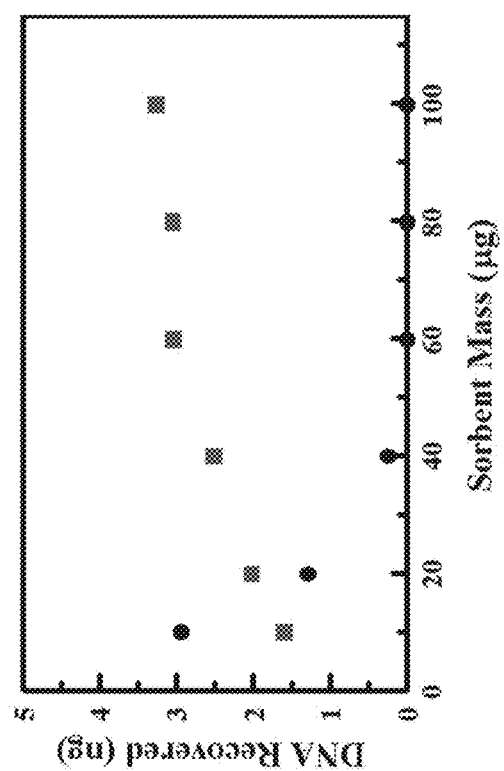
FIGS. 7A and 7B show the binding and recovery of DNA from a complex solution. DNA bound by (A) and recovered from (B) N5 (black circle) and CuEDA (red square) from bacterial lysis solution.
Figure 7A:
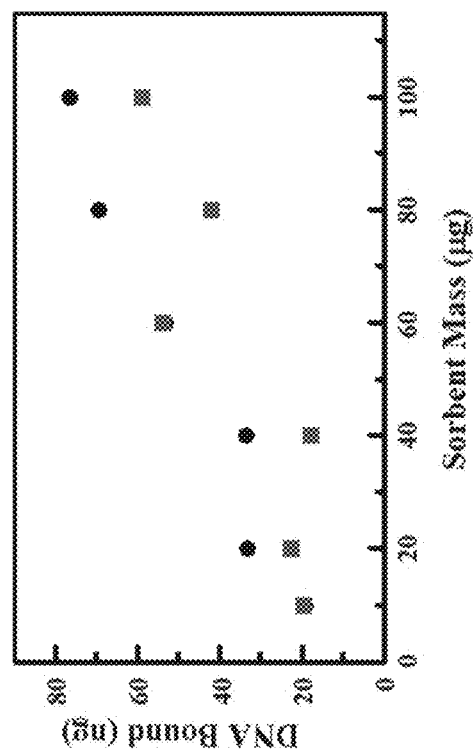

Based on the performance of the sorbents as described in the sections focused on adsorption, elution, and stabilization, the N5 and CuEDA sorbents were selected for the initial demonstration. FIGS. 7A and 7B show the DNA bound from the lysis solution using the two materials as well as the amount recovered from the sorbents. Both sorbents bound significant percentages of the total DNA available (N5 100% at 100 μg). Recovery of target in this study was impacted by the use of large sorbent concentrations in small volumes of eluent (100 μg in 100 μL; 100 mM TRIS/0.1% SDS).

CONCLUDING REMARKS

Sorbent materials of the type described here provide the potential for capture and stabilization of nucleic acids using a single material. This can be accomplished from complex solutions eliminating the need for purification steps. The sorbents offer a combination of stabilization compounds that are covalently linked to the sorbent. In this way, the compounds provide the necessary activity without the issue of downstream contamination for follow-on applications and with no loss of stabilizing compounds regardless of the complexity of the matrix in which they are used. The sorbent materials are reusable.

All documents mentioned herein are hereby incorporated by reference for the purpose of disclosing and describing the particular materials and methodologies for which the document was cited.

Although the present invention has been described in connection with preferred embodiments thereof, it will be appreciated by those skilled in the art that additions, deletions, modifications, and substitutions not specifically described may be made without departing from the spirit and scope of the invention. Terminology used herein should not be construed as being "means-plus-function" language unless the term "means" is expressly used in association therewith.

REFERENCES (1) Frippiat, C.; Zorbo, S.; Leonard, D.; Marcotte, A.; Chaput, M.; Aelbrecht, C.; Noel, F. Forensic Sci. Int.-Genet. 2011, 5, 386-392.

(2) Shabihkhani, M.; Lucey, G. M.; Wei, B. W.; Mareninov, S.; Lou, J. J.; Vinters, H. V.; Singer, E. J.; Cloughesy, T. F.; Yong, W. H. Clinical Biochemistry 2014, 47, 258-266.

(3) Blow, J. A.; Mores, C. N.; Dyer, J.; Dohm, D. J. J Virol Methods 2008, 150, 41-44.

(4) Garcia, A. H. Journal of Biosciences 2011, 36, 939-950.

(5) Block, W.; Smith, R. I. L.; Kennedy, A. D. Biol. Rev. 2009, 84, 449-484.

(6) Clermont, D.; Santoni, S.; Saker, S.; Gomard, M.; Gardais, E.; Bizet, C. Biopreserv. Biobank. 2014, 12, 176-183.

(7) Bonnet, J.; Colotte, M.; Coudy, D.; Couallier, V.; Portier, J.; Morin, B.; Tuffet, S. Nucleic Acids Research 2010, 38, 1531-1546.

(8) Brus, C.; Kleemann, E.; Aigner, A.; Czubayko, F.; Kissel, T. Journal of Controlled Release 2004, 95, 119-131.

(9) Kuo, J.-H. S.; Hwang, R. J Pharmacy Pharmacology 2004, 56, 27-33.

(10) Hernandez, G. E.; Mondala, T. S.; Head, S. R. Biotechniques 2009, 47, 667-+.

(11) Li, W.; Szoka, F. C., Jr. Pharmaceutical Research 2007, 24, 438-449.

(12) Wan, E.; Akana, M.; Pons, J.; Chen, J.; Musone, S.; Kwok, P.-Y.; Liao, W. Current Issues in Molecular Biology 2010, 12, 135-141.

(13) Michaud, C. L.; Foran, D. R. Journal of Forensic Sciences 2011, 56, 846-852.

(14) Seutin, G.; White, B. N.; Boag, P. T. Can. J. Zool.-Rev. Can. Zool. 1991, 69, 82-90.

(15) Allen-Hall, A.; McNevin, D. Forensic Sci. Int.-Genet. 2012, 6, 653-657.

(16) Rissanen, A. J.; Kurhela, E.; Aho, T.; Oittinen, T.; Tiirola, M. Applied Microbiology and Biotechnology 2010, 88, 977-984.

(17) Tuttle, R. M.; Waselenko, J. K.; Yosseffi, P.; Weigand, N.; Martin, R. K. Diagnostic Molecular Pathology 1998, 7, 302-309.

(18) Vonhippel, P. H.; Wong, K. Y. Science 1964, 145, 577-&.

(19) Whittier, C. A.; Horne, W.; Slenning, B.; Loomis, M.; Stoskopf, M. K. Journal of Virological Methods 2004, 116, 11-17.

(20) Fregeau, C. J.; Vanstone, H.; Borys, S.; McLean, D.; Maroun, J. A.; Birnboim, H. C.; Fourney, R. M. Journal of Forensic Sciences 2001, 46, 1180-1190.

(21) Vincek, V.; Nassiri, M.; Nadji, M.; Morales, A. R. Laboratory Investigation 2003, 83, 1427-1435.

(22) Crowe, J. H.; Carpenter, J. F.; Crowe, L. M. Annu. Rev. Physiol. 1998, 60, 73-103.

(23) Andrisin, T. E.; Humma, L. M.; Johnson, J. A. Pharmacotherapy 2002, 22, 954-960.

(24) Bachoon, D. S.; Chen, F.; Hodson, R. E. FEMS Microbiology Letters 2001, 201, 127-132.

(25) Blacksell, S. D.; Khounsy, S.; Westbury, H. A. Journal of Virological Methods 2004, 118, 33-37.

(26) Brannon-Peppas, L.; Ghosn, B.; Roy, K.; Cornetta, K. Pharmaceutical Research 2007, 24, 618-627.

(27) Chacko, R. T.; Ventura, J.; Zhuang, J. M.; Thayumanavan, S. Advanced Drug Delivery Reviews 2012, 64, 836-851.

(28) Coller, J. M.; Gray, N. K.; Wickens, M. P. Genes & Development 1998, 12, 3226-3235.

(29) Florell, S. R.; Coffin, C. M.; Holden, J. A.; Zimmermann, J. W.; Gerwels, J. W.; Summers, B. K.; Jones, D. A.; Leachman, S. A. Modern Pathology 2001, 14, 116-128.

(30) Krafft, A. E.; Russell, K. L.; Hawksworth, A. W.; McCall, S.; Irvine, M.; Daum, L. T.; Connoly, J. L.; Reid, A. H.; Gaydos, J. C.; Taubenberger, J. K. J. Clin. Microbiol. 2005, 43, 1768-1775.

(31) Ma, W. C.; Wang, M.; Wang, Z. Q.; Sun, L. H.; Graber, D.; Matthews, J.; Champlin, R.; Yi, Q.; Orlowski, R. Z.; Kwak, L. W.; Weber, D. M.; Thomas, S. K.; Shah, J.; Komblau, S.; Davis, R. E. Cancer Epidemiology Biomarkers & Prevention 2010, 19, 2445-2452.

(32) Ryu, J. H.; Chacko, R. T.; Jiwpanich, S.; Bickerton, S.; Babu, R. P.; Thayumanavan, S. Journal of the American Chemical Society 2010, 132, 17227-17235.

(33) Terui, Y.; Ohnuma, M.; Hiraga, K.; Kawashima, E.; Oshima, T. Biochemical Journal 2005, 388, 427-433.

(34) Tribioli, C.; Lufkin, T. J Biomol Tech 2006, 17, 249-251.

(35) Wolf, S. G.; Frenkiel, D.; Arad, T.; Finkel, S. E.; Kolter, R.; Minsky, A. Nature 1999, 400, 83-85.

(36) Kabanov, A. V.; Vinogradov, S. V. Angewandte Chemie-International Edition 2009, 48, 5418-5429.

(37) Khosravi-Darani, K.; Pardakhty, A.; Honarpisheh, H.; Rao, V.; Mozafari, M. R. Micron 2007, 38, 804-818.

(38) Lengsfeld, C. S.; Manning, M. C.; Randolph, T. W. Current Pharma Biotech 2002, 3, 227-235.

(39) Tan, M. L.; Choong, P. F. M.; Dass, C. R. Journal of Pharmacy and Pharmacology 2009, 61, 131-142.

(40) Xu, L.; Anchordoquy, T. Journal of Pharmaceutical Sciences 2011, 100, 38-52.

(41) Stevenson, H. S.; Wang, Y.; Muller, R.; Edelman, D. C. Biopreserv. Biobank. 2015, 13, 114-122.

(42) Roder, B.; Furuhwirth, K.; Vogle, C.; Wagner, M.; Rossmanith, P. J Clin Microbiol 2010, 48, 4260-4262.

(43) Miyamoto, T.; Okano, S.; Kasai, N. Biotechno Prog 2009, 25, 1675-1685.

(44) Foged, C.; Nielsen, H. M.; Frokjaer, S. Int J Pharm 2007, 331, 160-166.

(45) Workman, H.; Flynn, P. F. J Amer Chem Soc 2009, 131, 3806-3807.

(46) Kataoka, K.; Itaka, K.; Nishiyama, N.; Yamasaki, Y.; Oishi, M.; al., e. In Nucleic Acids Symp Ser; Oxford. 2005, pp 17-18.

(47) Oishi, M.; Nagasaki, Y.; Itaka, K.; Nishiyama, N.; Kataoka, K. J Am Chem Soc 2005, 127 1624-1625.

(48) Kasahara, T.; Miyazaki, T.; Nitta, H.; Ono, A.; Miyagishima, T.; al., e. J Toxicol Sci 2006, 31, 509-519.

(49) Melde, B. J.; Johnson, B. J.; Dinderman, M. A.; Deschamps, J. R. Microporous and Mesoporous Materials 2010, 130, 180-188.

(50) Foged, C.; Nielsen, H. M.; Frokjaer, S. J Liposome Res 2007, 17, 191-196.

(51) Hartmann, M. Chem Mater 2005, 17, 4577-4593.

(52) Sun, J. M.; Zhang, H.; Tian, R. J.; Ma, D. D.; Bao, X. H.; al., e. Chem Comm 2006, 1322-1324.

(53) Slowing, I. I.; Trewyn, B. G.; Lin, V. S. Y. J Am Chem Soc 2007, 129, 8845-8849.

(54) Fuertes, A. B.; Valle-Vigon, P.; Sevilla, M. J Colloid Int Sc 2010, 349, 173-180.

(55) Trewyn, B. G.; Slowing, I. I.; Giri, S.; Chen, H. T.; Lin, V. S. Y. Acc. Chem. Res. 2007, 40, 846-853.

(56) Slowing, I I; Trewyn, B. G.; Gin, S.; Lin, V. S. Y. Advanced Functional Materials 2007, 17, 1225-1236.

(57) Rosenhold, J.; Sahlgren, C.; Linden, M. J Mater Chem 2010, 20, 2707-2713.

(58) Rosenholm, J. M.; Sahlgren, C.; Linden, M. Nanoscale 2010, 2, 1870-1883.

(59) Gao, F.; Botella, P.; Corma, A.; Blesa, J.; Dong, L. J Phys Chem B 2009, 113, 1796-1804.

(60) Ashley, C. E.; Carnes, E. C.; Epler, K. E.; Padilla, D. P.; Phillips, G. K.; Castillo, R. E.; Wilkinson, D. C.; Wilkinson, B. S.; Burgard, C. A.; Kalinich, R. M.; Townson, J. L.; Chackerian, B.; Willman, C. L.; Peabody, D. S.; Wharton, W.; Brinker, C. J. Acs Nano 2012, 6, 2174-2188.
(61) Li, Z.; Barnes, J. C.; Bosoy, A.; Stoddart, J. F.; Zink, J. I. Chemical Society Reviews 2012, 41, 2590-2605.
(62) Johnson, B. J.; Melde, B. J.; Dinderman, M. A.; Lin, B. C. Plos One 2012, 7.
(63) Wang, F.; Guo, C.; Yang, L. R.; Liu, C. Z. Bioresource Technol 2010, 101, 8931-8935.
(64) Lin, B.; Johnson, B. J.; Melde, B. J.; Haas, G. M.; McConner, M. K. J.; Taft, J. R. Open Access Journal of Science and Technology 2015, submitted.
(65) Johnson, B. J.; Melde, B. J.; Peterson, G. W.; Schindler, B. J.; Jones, P. Chemical Engineering Science 2012, 68, 376-382.
(66) Amatani, T.; Nakanishi, K.; Hirao, K.; Kodaira, T. Chem. Mater. 2005, 17, 2114-2119.
(67) Nakanishi, K.; Amatani, T.; Yano, S.; Kodaria, T. Chem Mater 2008, 20, 1108-1115.
(68) Johnson, B. J.; Leska, I. A.; Melde, B. J.; Siefert, R. L.; Malanoski, A. P.; Moore, M. H.; Taft, J. R.; Deschamps, J. R. Materials 2013, 6, 1403-1419.
(69) Burleigh, M. C.; Dai, S.; Hagaman, E. W.; Lin, J. S. Chem. Mater. 2001, 13, 2537-2546.
(70) Zhu, H. G.; Jones, D. J.; Zajac, J.; Dutartre, R.; Rhomari, M.; Roziere, J. Chemistry of Materials 2002, 14, 4886-4894.
(71) White, B. J.; Melde, B. J.; Peterson, G. W., Functionalized organosilicate sorbents for air purification; NRL Formal Report #NRL/FR/6920—13-10,251; US Naval Research Laboratory: 2013.
(72) Venner, H.; Zimmer, C. Biopolymers 1966, 4, 321-&.
(73) Kim, H. J.; Guiochon, G. Anal Chem 2005, 77, 93-102.
(74) Umpleby, R. J.; Baxter, S. C.; Bode, M.; Berch, J. K.; Shah, R. N.; Shimizu, K. D. Anal Chim Acta 2001, 435, 35-42.
(75) Johnson, B. J.; Melde, B. J.; Charles, P. T.; Dingerman, M. A.; Malanoski, A. P.; Leska, I. A.; Qadri, S. B. Talanta 2010, 81, 1454-1460.
(76) Moran, M. C.; Miguel, M. G.; Lindman, B. Biomacromolecules 2007, 8, 3886-3892.
(77) Li, X.; Zhang, J.; Gu, H. Langmuir 2012, 28, 2827-2834.
(78) Masotti, A.; Bordi, F.; Ortaggi, G.; Marino, F.; Palocci, C. Nanotechnology 2008, 19.
(79) Wu, S.; Huang, X.; Du, X. Angewandte Chemie-International Edition 2013, 52, 5580-5584.
(80) Pu, F.; Liu, Z.; Ren, J.; Qu, X. Chemical Communications 2013, 49, 2305-2307.
(81) Correa, A. d. A.; Miagostovich, M. P. Food and Environmental Virology 2013, 5, 144-149.

What is claimed is:

1. A method of storing a nucleic acid comprising: contacting the nucleic acid with a mesoporous ethane-bridged silica sorbent with both N5 and CuEDA, thereby causing the nucleic acid to releasably bind to the sorbent.

2. The method of claim 1, further comprising an initial step of washing the sorbent with a detergent prior to said contacting.

3. The method of claim 1, further comprising a step of eluting the nucleic acid from the sorbent following binding.

4. The method of claim 1, wherein said contacting occurs in a complex matrix comprises lysed cells.

5. The method of claim 1, wherein said nucleic acid comprises RNA.

6. The method of claim 1, wherein said sorbent is associated with a stabilizer.

7. The method of claim 6, wherein said stabilizer is selected from the group consisting of bovine serum albumin, trehalose, and glucosamine.

* * * * *